(12) United States Patent
Eilertsen et al.

(10) Patent No.: US 10,034,984 B2
(45) Date of Patent: Jul. 31, 2018

(54) INJECTION NEEDLE HAVING SHIELD ACTIVATED VALVE

(71) Applicant: Novo Nordisk A/S, Bagsvaerd (DK)

(72) Inventors: Lars Eilertsen, Fredensborg (DK); Henrik Bengtsson, Taastrup (DK)

(73) Assignee: Novo Nordisk A/S, Bagsværd (DK)

( * ) Notice: Subject to any disclaimer, the term of this patent is extended or adjusted under 35 U.S.C. 154(b) by 0 days.

(21) Appl. No.: 14/767,308

(22) PCT Filed: Feb. 14, 2014

(86) PCT No.: PCT/EP2014/052902
§ 371 (c)(1),
(2) Date: Aug. 12, 2015

(87) PCT Pub. No.: WO2014/125067
PCT Pub. Date: Aug. 21, 2014

(65) Prior Publication Data
US 2016/0001014 A1    Jan. 7, 2016

Related U.S. Application Data

(60) Provisional application No. 61/767,822, filed on Feb. 22, 2013.

(30) Foreign Application Priority Data

Feb. 18, 2013   (EP) ..................................... 13155603

(51) Int. Cl.
*A61M 5/32*     (2006.01)
*A61M 5/34*     (2006.01)
(Continued)

(52) U.S. Cl.
CPC ............. *A61M 5/346* (2013.01); *A61M 5/326* (2013.01); *A61M 5/3291* (2013.01); *A61M 5/001* (2013.01);
(Continued)

(58) Field of Classification Search
CPC .. A61M 2005/3128; A61M 2005/3267; A61M 2005/3268; A61M 2005/3253
See application file for complete search history.

(56) References Cited

U.S. PATENT DOCUMENTS 2,653,607 A      9/1953   Deans
4,416,663 A  *  11/1983   Hall ...................... A61M 5/326
                                                                  604/198

(Continued)

FOREIGN PATENT DOCUMENTS

CN      1139010 A     1/1997
CN      1665558 A     9/2005
(Continued)

*Primary Examiner* — Deanna K Hall
(74) *Attorney, Agent, or Firm* — Wesley Nicholas

(57) ABSTRACT

The present invention relates to a needle assembly having a build-in valve (30). The needle assembly is built up from a hub (20) carrying a needle cannula (10) and a telescopically movable shield (40) which axially covers the distal tip (13) of the needle cannula (10) between injections. The valve (30) is operated by the shield (40) and is arranged such that it is closed when the distal tip (13) of the needle cannula (10) is covered by the shield (40) and is opened when the telescopically movable shield (40) has been retracted a specific distance (X) proximally to the distal tip (13) of the distal cannula part (11).

5 Claims, 3 Drawing Sheets

(51) Int. Cl.
*A61M 5/00* (2006.01)
*A61M 5/31* (2006.01)

(52) U.S. Cl.
CPC ............... *A61M 2005/3118* (2013.01); *A61M 2005/3128* (2013.01); *A61M 2005/3267* (2013.01)

(56) References Cited

U.S. PATENT DOCUMENTS

| | | | |
|---|---|---|---|
| 5,626,567 A | 5/1997 | Gmeiner | |
| 2013/0018310 A1* | 1/2013 | Boyd | A61M 5/2448 604/110 |
| 2013/0018323 A1* | 1/2013 | Boyd | A61M 5/2448 604/191 |

FOREIGN PATENT DOCUMENTS

| | | |
|---|---|---|
| EP | 1536854 A1 | 6/2005 |
| JP | 2002501398 A | 1/2002 |
| WO | 96/11028 A1 | 4/1996 |
| WO | 2011095478 A1 | 8/2011 |
| WO | 2011095483 A1 | 8/2011 |
| WO | 2011095486 A1 | 8/2011 |
| WO | 2012059449 A1 | 5/2012 |

\* cited by examiner

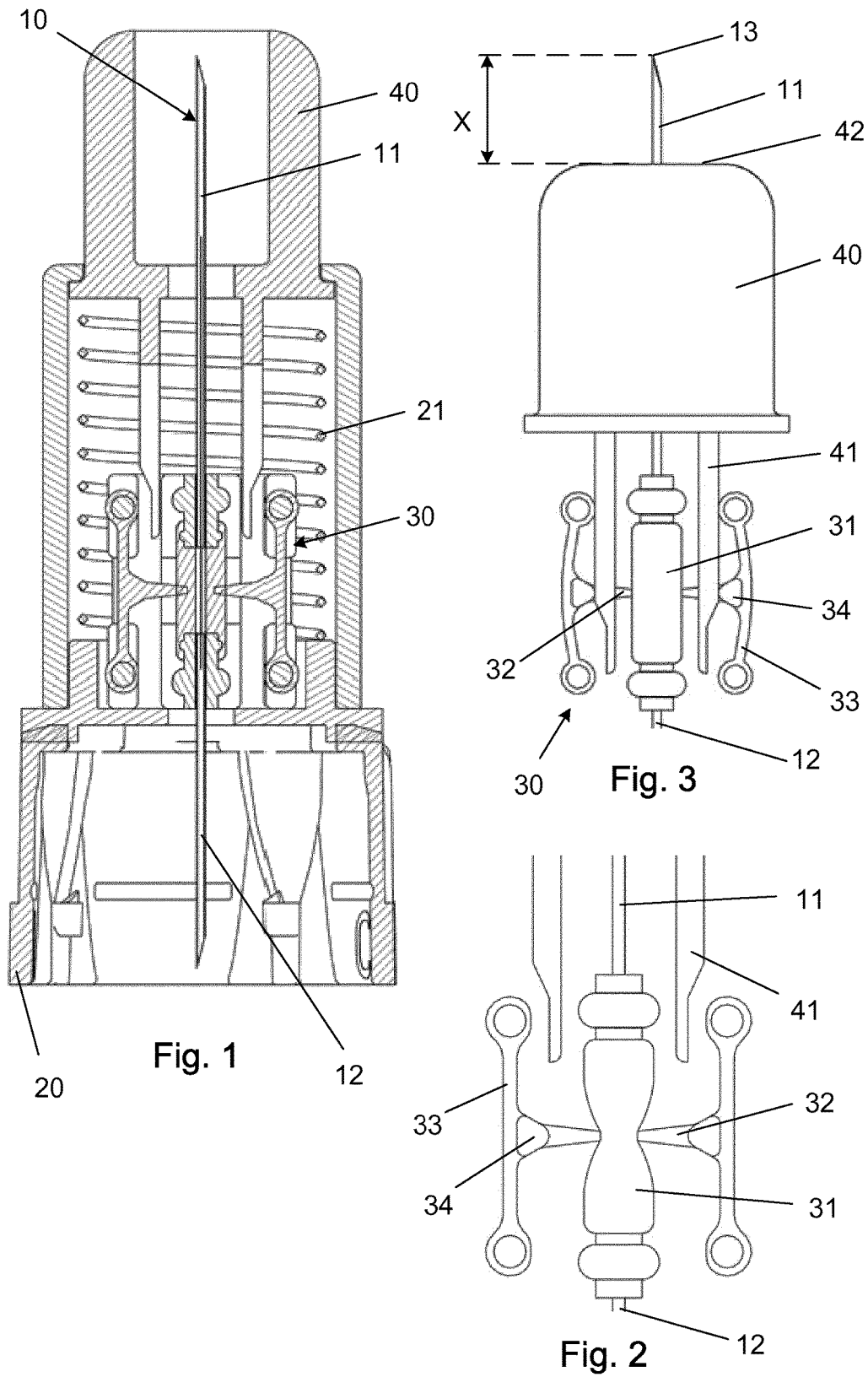

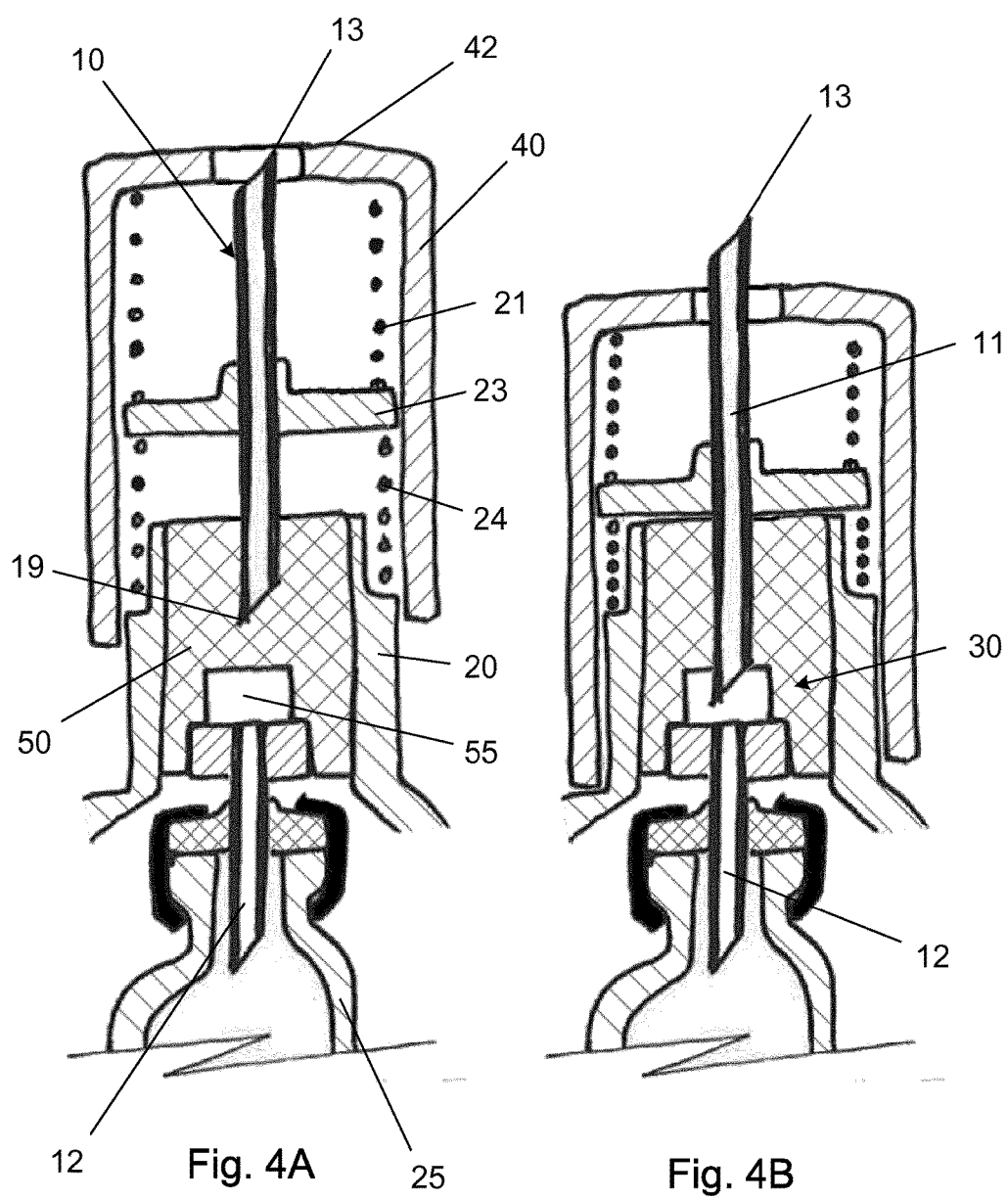

INJECTION NEEDLE HAVING SHIELD ACTIVATED VALVE

CROSS-REFERENCE TO RELATED APPLICATIONS

This application is a 35 U.S.C. § 371 National Stage application of International Application PCT/EP2014/052902 (published as WO 2014/125067), filed Feb. 14, 2014, which claims priority to European Patent Application 13155603.7, filed Feb. 18, 2013; this application claims priority under 35 U.S.C. § 119 to U.S. Provisional Application 61/767,822; filed Feb. 22, 2013.

THE TECHNICAL FIELD OF THE INVENTION

The invention relates to a shielded injection needle in which a telescopically shield covers the sharp end of a needle cannula between injections and especially to such shielded injection needles wherein the telescopically movement of the shield activates a valve which closes for liquid passage through the lumen of the needle cannula.

DESCRIPTION OF RELATED ART

An injection needle having a valve preventing flow through the lumen of the needle cannula in one direction is disclosed in WO 96/11028. A similar pen needle assembly having a valve is disclosed in U.S. Pat. No. 5,626,567.

A needle system having an on/off valve which can open and close the flow through the lumen of the needle cannula in dependency of the movement of a shield is disclosed in WO12/059449, FIG. 4. In this needle system the seal which cut off the flow through the needle cannula is carried by a telescopically shield which shields the sharp end of the needle cannula between injections. It is a drawback with such solution that the liquid drug can keep flowing through the lumen of the needle cannula even after the distal tip of the needle cannula has been removed from the skin of the user.

DESCRIPTION OF THE INVENTION

It is an object of the present invention to provide a shielded needle assembly with a valve arrangement, which valve arrangement shuts off the liquid flow through the lumen of the needle cannula before the distal tip of the needle cannula is pulled clear of the skin of the user.

The invention is defined in the attached claim 1 followed by a number of embodiments. The individual claims are explained in details in the following.

Accordingly, in one aspect of the present invention, the needle assembly comprises the following main components:
  A hub carrying connecting means for connecting the hub to an injection device.
  A needle cannula which has a distal part for penetrating the skin of the user, and a proximal part for penetrating into a drug compartment in the injection device. The distal part and the proximal part can be separate needle cannulae or they can form parts of one uniform needle cannula.
  A shield which is able to move telescopically in relation to the hub. The shield either slides on the outside of the hub or internally in the hub.
  A valve arrangement for shutting off flow through the lumen of the needle cannula.

The shield slides telescopically i.e. axially between two different positions:
  a first position wherein the shield axially covers the distal tip of the distal cannula part, and
  a second position wherein the shield is axially retracted proximally to the distal tip of the distal cannula part.

By the term "axially covers" in the first position is meant that the shield cover the distal tip of the needle cannula when viewed from the side. An opening in the shield is present such that the shield can be retracted to a position in which the distal tip of the needle cannula extends through that opening in front of the shield.

The valve arrangement is arranged such that the flow is shut off when the shield is in its first position and flow through the lumen is allowed when the shield is in its second position.

The needle assembly is preferably for multiple use. By this means that the same needle cannula is used for several injections. The valve thus serves the purpose of preventing the liquid inside the lumen of the needle cannula and inside the system from drying and thus clogging the system. Such needle assembly with a valve is therefore excellent for keeping the lumen of the needle cannula free of any dried remains which could potentially clogg the needle cannula.

The opening of the valve arrangement is arranged such that shield activates the valve to open when the shield has been moved a certain distance proximally i.e. the distal tip of the needle cannula extends a certain distance beyond the shield. It is thereby ensured that the valve only opens when the tip of needle cannula is actually in the skin of the user. The same mechanisms are used vice versa to close the valve such that the valve closes before the tip of the needle cannula is removed from the skin.

By ensuring that the lumen through the needle cannula is only open when the tip of needle cannula is actually inside the skin of the user contamination of the compartment containing the liquid drug from the outside through the lumen can be avoided.

In a further embodiments the two parts making up the needle cannula is formed as separate individual needle cannulae. These parts can be connected in multiple ways as will be explained.

The distal part and the proximal part are preferably separated by a flexible tube which together with the two needle parts can be carried by the hub.

When the flexible tube is compressed flow through the tube and thus the needle cannula is prevented whereas when the compression is removed flow is allowed. The shield is formed such that the valve mechanism compresses the flexible tube thus preventing flow when the shield is in its first position i.e. the position in which the distal tip of the needle cannula is covered. Once the shield is moved into the second position the compression is removed thereby allowing the liquid drug to flow freely through the lumen of the needle cannula.

However, in one embodiment, the flexible tube is pre-compressed such that even in the second position of the shield the liquid drug does not flow entirely freely but only flows when the pressure in the drug compartment is over a certain level. In this way it is assured that the liquid drug only flows as a result of an injection force being applied to the liquid drug.

The pre-compression can either be created internally in the material making up the flexible tube or it can be provided by mechanical means pressing on the flexible tube.

Alternatively the separate distal cannula part and the separate second cannula part can be connected via chamber housed in the hub. The chamber can be an integral part of the shield or it can be provided in an insert inserted in the shield. The proximal cannula part is constantly in connection with the chamber whereas the distal cannula part moves with the shield between a position in which it is connected to the chamber and a position in which it is disconnected from the chamber i.e. an open position and a closed position of the valve arrangement.

In the position where the distal cannula part is connected to the chamber liquid flow is possible from the drug compartment in the injection device via the proximal cannula part and into the chamber and from there via the distal cannula part and into the skin of the user.

In an embodiment, the two parts making up the needle cannula are formed as parts of one uniform needle cannula. As also depicted in the accompanying drawings, the needle cannula can be one and the same uniform cannula such that the distal half makes up the distal part and the proximal half makes up the proximal end. However, these parts are not necessarily restricted to exact halves.

Further this uniform needle cannula comprises a distal radial opening formed as a hole radially through the sidewall of the needle cannula and a similar proximal radial opening.

The distal radial opening connects to a distal lumen and the proximal radial opening connects to a proximal lumen. The distal lumen and the proximal lumen are preferably separated by a lumen blocking part such as a weld, a compression of the cannula or an insert provided inside the lumen and preventing liquid flow through the lumen.

The telescopically movable shield is preferably provided with means for generating a liquid passage-way from the proximal radial opening to the distal radial opening when slided axially such that the liquid drug can flow from the proximal lumen and into the distal lumen. This passage-way is preferably formed as a chamber provided in the shield and preferably in an insert connected to, or inserted in, the telescopically movable shield.

The insert carrying the chamber is preferably made from a rubber material. The insert blocking the passage through the lumen of the uniform needle cannula could also be formed from a rubber material.

In all the described embodiments the telescopic shield could also carry a reservoir in which the tip of the distal cannula part is maintained and cleaned during or between injection(s), such as it is e.g. described in International patent application No.: PCT/EP2013/072064, or its U.S. counterpart U.S. Patent Application Publication US 2015/0273161.

Definitions:

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

A "uniform needle cannula" is meant to cover a needle cannula manufactured in one single piece. Metallic needle cannulae ares usually produced as drawn metal tubes. In that respect uniform means one single piece of tubing.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle assemblies specially designed for pen injections systems are defined in ISO standard No. 11608, part 2, and are often referred to as "pen needles". Pen needles have a front-end for penetrating into the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible'can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1 shows a cross-sectional view of the shielded injection needle.

FIG. 2 shows a view of the valve arrangement in the closed position.

FIG. 3 shows a view of the valve arrangement in the open position.

FIG. 4A-B shows a view of a further embodiment of the shielded needle cannula.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figures 5A, 5B:
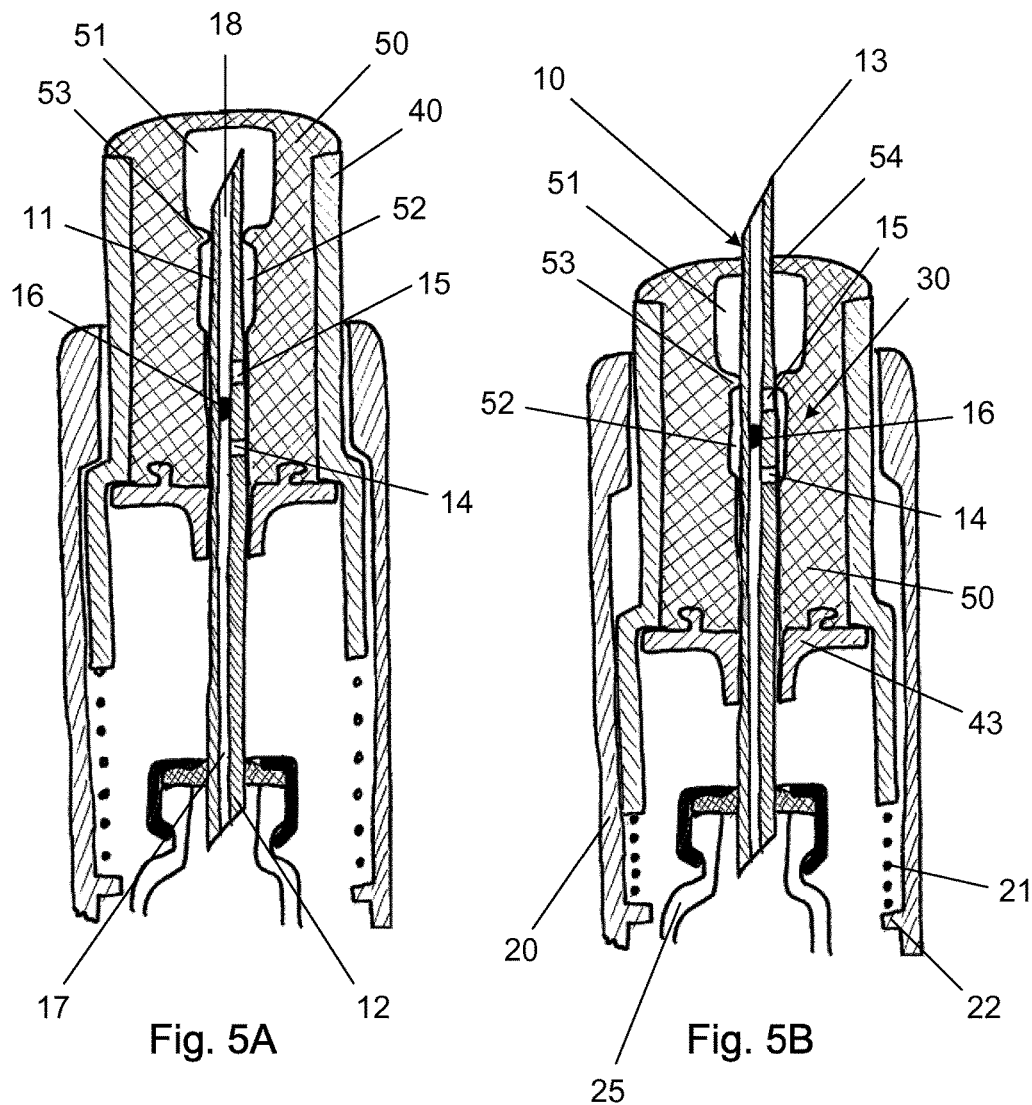
FIG. 5A-B Shows a view of an embodiment having a uniform needle cannula.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula penetrating the skin of the user during injection whereas the term "proximal end" is meant to refer to the opposite end pointing away from the user and used to penetrate the cartridge in the injection device to which the needle assembly is attached.

In the different embodiments disclosed, the same elements are identified by the same reference numbers. The major elements being; A needle cannula 10, a hub 20, a valve 30, a movable shield 40, and an insert 50.

FIG. 1 discloses an embodiment having a build in valve arrangement 30 which is disclosed in further details in FIGS. 2 and 3.

The needle cannula 10 has a distal part 11 and a proximal part 12 both secured to the hub 20 and connected to each other through a flexible tube 31 which flexible tube 31 constitutes a part of the valve arrangement 30 as shown in FIG. 2-3.

The valve arrangement 30 comprises a number of squeeze arms 32 which are able to squeeze the flexible tube 31 such that the liquid drug cannot flow through the lumen of the flexible tube 31. These squeeze arms 32 are provided on suspended bridge parts 33 which are also secured to the hub 20.

When the bridge part 33 is in a situation of rest as disclosed in FIG. 2, the squeeze arms 32 squeezes the flexible tube 31 such that the valve arrangement 30 in this position is closed. All though the figures only disclose two such bridge arms 33 any number can be provided for.

The radial movement of these squeeze arms 32 are controlled by the axial movement of the shield 40. The shield 40 is urged in the distal direction by a first compression spring 21 which is located between the hub 20 and the shield 40. The spring 21 can be made as a separate metallic spring or it can alternatively be formed as a plastic spring moulded integral with e.g. the hub 20. The shield 40 is further provided with a plurality of axially extending arms 41. When the shield 40 is moved proximally during injection as disclosed in FIG. 3 these axially extending arms 41 activates the bridge part 33 via an actuation member 34 whereby the bridge part 33 flex away from is axial rest position. The squeeze arms 32 moves together with the bridge part 33 to a position in which the squeeze arms 32 does not compress the flexible tube 31 thus allowing the liquid drug to flow freely through the flexible tube 31.

As best seen in FIG. 3, the valve arrangement 30 opens once the shield 40 has been moved a predetermined distance (X) in the proximal direction and the axially extending arms 41 of the shield 40 moves the squeeze arms 32 radially. The result being that the valve arrangement 30 is opened and respectively closed only when the distal tip 13 of the needle cannula 10 is the same predetermined distance (X) inside the body of the user as the distal surface 42 of the shield 40 abuts the body of the user during injection.

When the distal tip 13 of the distal part 11 is removed from the object, the spring 21 urges the movable shield 40 into its first position in which it covers the distal tip 13. During retraction of the needle cannula 10 from the body of the user, the valve arrangement 30 shuts off the liquid flow through the lumen of the needle cannula 10 when the distal surface 42 of the shield 40 has passed the predetermined distance (X) from the tip 13 of the needle cannula 10 moving towards the distal tip 13.

A different embodiment is disclosed in FIG. 4A-B.

The needle cannula 10 is also here separated into two parts, a distal part 11 and a proximal part 12. The proximal part 12 is secured to the hub 20 and penetrates into the cartridge 25 when the needle assembly is attached to an injection device.

In this embodiment, the hub 20 further carries the insert 50 which insert 50 has one single chamber 55 into which the liquid drug flows whenever the proximal part 12 is located in liquid communication with the interior of the cartridge 25.

A needle shield 40 slides telescopically on the hub 20 and is urged in the distal direction by a spring 21. The distal part 11 is secured to a needle plate 23 which is urged in the distal direction by a second compression spring 24 provided between the needle plate 23 and the hub 20.

The first position of the needle shield 40 is depictured in FIG. 4A. In this situation of rest, the first spring 21 urges the shield 40 in the distal direction such that the shield 40 covers the distal end 13 of the distal part 11 and the second spring 24 urges the distal part 11 in the distal direction such that the proximal end 19 of the distal part 11 is located distally to the single chamber 55 and concealed within the insert 50. In this situation the valve arrangement 30 is shut.

In the second position wherein the user performs an injection, the distal surface 42 of the shield 40 is pressed in the proximal direction by the impact with the skin of the user. Once the first spring 21 is compressed, the needle plate 23 and with it the distal part 11 is moved in the proximal direction against the bias of the second spring 24. During this proximally movement of the distal part 11 the proximal end 19 of the distal part 11 is moved into the single chamber 55 thereby creating a liquid flow from the interior of cartridge 25 and into the skin of the user. The valve arrangement 30 is thus open.

FIG. 5A-B discloses a different embodiment in which the distal part 11 and the proximal part 12 are uniform such that they form part of one and the same needle cannula 10. The needle cannula 10 is secured to the hub 20.

The needle cannula 10 is provided with two radial openings 14, 15; a proximal opening 14 and a distal opening 15. The lumen of the needle cannula 10 is blocked by an insert 16 which divides the lumen into a proximal lumen 17 and a distal lumen 18. The proximal lumen 17 is, in operation, in contact with the liquid drug inside the cartridge 25, however the insert 16 prevents the liquid drug to flow from the proximal lumen 17 and into the distal lumen 18. The distal opening 14 forms a liquid communication with the distal lumen 17 and the proximal opening 15 form a liquid communication with the distal lumen 18.

The shield 40 which is urged in the distal direction by the spring 21 encompassed between the shield 40 and a ridge 22 provided on the hub 20, carries an insert 50. The insert 50 is preferably made from a rubber material in order to obtain an adequate liquid seal against the needle cannula 10.

The insert 50 can be formed integral with the shield 40 or alternatively it can be a separate insert 50, which, as disclosed in FIG. 5A-B, are connected to a plate 43 which is then attached to the shield 40.

The insert 50 is provided with a distal chamber 51 and a proximal chamber 52. These two chambers 51, 52 are separated by a flange 53 which slides on the needle cannula 10 in a liquid tight seal.

In one embodiment the distal chamber 51 contains an antiseptic liquid suitable for keeping the distal tip 13 of the needle cannula 10 sterile or at least clean.

The proximal chamber 52 is empty and is in the non-use situation (disclosed in FIG. 5A) located in a position distal to the distal opening 15 in the needle cannula 10. In this situation, the tip 13 of the needle cannula 10 is located inside the distal chamber 51. Further, the proximal chamber 52 has a length sufficient for it to axially connect the distal opening 14 and the proximal opening 14 in order to form a liquid flow-way between the two openings 14, 15.

During injection, as disclosed in FIG. 5B, the shield 40 together with the insert 50 is slided in the proximal direction against the bias of the spring 21 such that the distal tip 13 of the needle cannula 10 penetrates through a distal end 54 of the insert 50. In this position, the proximal chamber 52 forms a liquid flow-way connecting the proximal opening 14 and the distal opening 15 thereby allowing the liquid drug to flow from the proximal lumen 17 and into the distal lumen 18, and ultimately to flow into the user.

Some preferred embodiments have been shown in the foregoing, but it should be stressed that the invention is not limited to these, but may be embodied in other ways within the subject matter defined in the following claims.

The invention claimed is:

1. A needle assembly having a built-in valve, comprising:
    a hub comprising structure for connecting the hub to an injection device,
    a proximal cannula part for penetrating into a reservoir containing a liquid drug,
    a distal cannula part having a distal tip for penetrating the skin of an object,
    a telescopically movable shield which is movable relative to the hub between:
        a first position wherein the shield axially covers the distal tip of the distal cannula part, and
        a second position wherein the shield is axially retracted proximally towards the proximal cannula part,
    a valve positioned between the proximal cannula part and the distal cannula part and which valve is closed when the telescopically movable shield is in the first position and open when the telescopically movable shield is in the second position such that the valve is opened when the telescopically movable shield has been retracted a specific distance (X) proximally to the distal tip of the distal cannula part, and
    wherein the needle assembly is multiple usable such that the same distal needle cannula part is used for several injections and the telescopically movable shield carries a reservoir containing an antiseptic liquid in which the distal tip of the distal cannula part is maintained and cleaned between injections.

2. A needle assembly according to claim 1, wherein the distal cannula part and the proximal cannula part are separate cannulae.

3. A needle assembly according to claim 2, wherein the distal part and the proximal part are connected by a flexible tube.

4. A needle assembly according to claim 3, wherein the distal part, the proximal part and the flexible tube are carried by the hub.

5. A needle assembly according to claim 3, wherein the valve compresses the flexible tube when the telescopically movable shield is in the first position.

* * * * *